Figure 1:
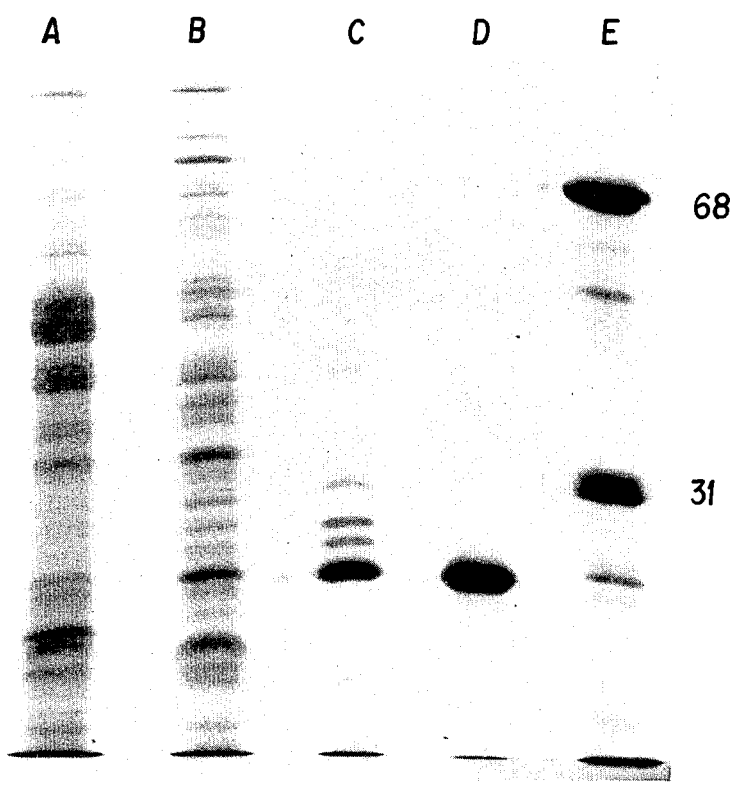

United States Patent [19]

Obrig

[11] Patent Number: 4,921,841
[45] Date of Patent: May 1, 1990

[54] IMMUNOAFFINITY PURIFICATION OF PHYTOLACCIN PROTEINS AND THEIR USE IN TREATING HERPES SIMPLEX VIRUS TYPE II

[76] Inventor: Thomas G. Obrig, 23 Burhans Pl., Delmar, N.Y. 12054

[21] Appl. No.: 929,878

[22] Filed: Nov. 13, 1986

Related U.S. Application Data

[62] Division of Ser. No. 449,769, Dec. 14, 1982, Pat. No. 4,672,053.

[51] Int. Cl.$^5$ ...................... A61K 37/48; A61K 37/00
[52] U.S. Cl. ........................................... 514/8; 514/2; 530/370; 530/412; 530/413; 424/94.1
[58] Field of Search .................... 514/2; 530/350, 370, 530/413; 435/68; 424/195.1

[56] References Cited

U.S. PATENT DOCUMENTS 4,341,761 7/1982 Garfield et al. ..................... 530/413

OTHER PUBLICATIONS

Irvin, J.D., *Arch Biochem Biophys*, vol. 169, pp. 522–528, 1975, "Purification and Partial Characterization of the Antiviral Protein from *Phytolacca americana* which inhibits Eukaryotic Protein Synthesis".

Irvin et al., *Arch Biochem Biophys*, vol. 200 (2), pp. 418–425, 1980, "Purification and Properties of a Second Antiviral Protein from *Phytolacca americana* which Inactivates Eukaryotic Ribosomes[1]".

Barbieri et al., *Biochem J*, vol. 203, pp. 55–59, 1982, "Purification and Partial Characterization of another form of the Activiral Protein from the Sedds of *Phytolacca americana* L.(epokeweed)".

Orbig et al., *Arch Biochem Biophys*, vol. 155, pp. 278–287, 1973, "The Effect of an Antiviral Peptide on the Ribosomal Reactions of the Peptide Elongation Enzymes, EF–I and EF–II".

*Primary Examiner*—Thomas G. Wiseman
*Attorney, Agent, or Firm*—Pennie & Edmonds

[57] ABSTRACT

Antiviral proteins phytolaccin$_1$ and phytolaccin$_2$ were isolated from the higher plant *Phytolaccin americana* using the technique of immunoaffinity chromatography. Phytolaccin proteins were purified to apparent homogeneity in a rapid and efficient chromatographic procedure utilizing immobilized monospecific anti-phytolaccin antibodies. Immunoaffinity-purified phytolaccin$_1$ and phytolaccin$_2$ were determined by denaturing gel electrophoresis to be of approximately 25,600 and 28,400 daltons, respectively. The two immunoaffinity-purified proteins were equally potent inhibitors of eukaryotic cell-free protein biosynthesis and exhibited mostly similar high-order UV derivative spectra. Antibodies against phytolaccin$_1$ and phytolaccin$_2$ did not cross-react with the heterologous antigen, indicating a structural dissimilarity between the two phytolaccin proteins.

11 Claims, 6 Drawing Sheets

Legend:

| | Virus | Drug |
|---|---|---|
| (———) | Yes | No |
| (xxxx) | No | Yes |
| (- - - -) | Yes | Yes |

IMMUNOAFFINITY PURIFICATION OF PHYTOLACCIN PROTEINS AND THEIR USE IN TREATING HERPES SIMPLEX VIRUS TYPE II

This is a division of application Ser. No. 449,769 filed Dec. 14, 1982 which issued to U.S. Pat. No. 4,672,053 on June 9, 1987.

TECHNICAL FIELD

This invention relates to a process for the purification of antiviral phytolaccin proteins from *Phytolaccin americana* by means of immunoaffinity chromatography. The invention also relates to a method for treating Herpes Simplex Virus type II using a phytolaccin protein purified according to the disclosed process.

BACKGROUND OF THE INVENTION

Phytolaccin, which, in the literature, has been referred to as PAP—*Phytolacca americana* protein—is a plant-derived proteinaceous toxin which inhibits protein biosynthesis. The biological properties of various plant toxins was a subject reviewed by Olsnes, S., and Pihl, A., in *Receptors and Recognition Series B: The Specificity and Action of Animal, Bacterial and Plant Toxins,* Cuatrecasas, ed., pp. 130–173, (Chapman and Hall, London, 1976). Phytolaccin has been found to demonstrate antiviral activity in plants, Duggar, B. M., and Armstrong, J. K., *Ann. Missouri Bot. Garden,* Vol. 12, pp. 359–366 (1925); Grogan, R. G., and Kimble, K. A., *Phytopathology,* Vol. 54, pp. 75–78 (1964).

The protein was first purified from Phytolacca sp. by Wyatt and Shepherd, see Phytopathology, Vol. 59, pp. 1787–1794 (1969) and subsequently, two forms of the protein were isolated and were determined to exhibit similar biological activities, Irvin, J. D., *Arch. Biochem. Biophys.,* Vol. 169, pp. 522–528 (1975); Irvin, J.D., Kelley, T. and Robertus, J. D. *Arch. Biochem. Biophys.,* Vol. 200, pp. 418–425 (1980).

Phytolaccin was the first of the plant-derived toxins shown to be a potent inhibitor of protein biosynthesis in eukaryotic cell-free systems, Obrig, T. G., Irvin, J. D., and Hardesty, B., *Arch. Biochem. Biophys.,* Vol. 155, pp. 278–289 (1973). At that time, it was concluded that inhibition appeared to involve a specific effect of the agent on the larger (60S) ribosomal subunit. Moreover, it was shown that maximum inhibition of protein synthesis occurred at a 1:10 molar ratio of inhibitor to ribosomes, suggesting that phytolaccin possessed enzymatic properties. The inhibitory action of phytolaccin was demonstrated to be directly on the ribosome, resulting in an altered functional interaction of ribosomes with elongation factors EF-1 and EF-2 . The nature of the ribosomal lesion caused by phytolaccin, however, remains to be elucidated.

To date, purification of phytolaccin from plants has been carried out by conventional methods of ion-exchange chromatography.

Herpes viruses are eukaryotic, DNA viruses. Known anti-herpetic agents include pharmaceuticals such as Acyclovir (Burroughs-Wellcome Co.) and Arildone (Sterling Drug Co.). The long-term effectiveness of these agents is in question, as clinical observations have indicated that the target virus can develop resistance to the drugs shortly after initiation of therapy.

SUMMARY OF THE INVENTION

The present invention relates to a method for the treatment of Herpes Simplex Virus type II infections in mammals by the administration of a therapeutically effective amount of $phytolaccin_1$ protein.

The invention also discloses an immunoaffinity isolation process for the rapid purification of phytolaccin proteins to apparent homogeneity using immobilized monospecific anti-phytolaccin antibodies. The process advantageously provides a highly purified product and permits the separation of antiviral proteins $phytolaccin_1$ and $phytolaccin_2$ from mixtures of phytolaccin proteins.

BRIEF DESCRIPTION OF THE FIGURES

FIG. 1 represents an SDS-PAGE analysis of $phytolaccin_1$ purified by a conventional ion-exchange chromatography technique. (A) crude leaf homogenate, (B) 40–100% ammonium sulfate fraction prepared from crude homogenate (C) DEAE cellulose fraction, (D) phosphocellulose fraction, (E) protein standards, $Mr \times 10^{-3}$.

FIG. 2 represents an SDS-PAGE analysis of (A) antibody to $phytolaccin_1$, and (B) $phytolaccin_1$ purified by the immunoaffinity process of the invention. Numbers are calculated mass of individual proteins $\times 10^{-3}$.

FIG. 3 represents an SDS-PAGE analysis of phytolaccins purified by a conventional ion-exchange chromatography technique; phosphocellulose column fractions. (A) protein standards of 31,000 and 68,000 molecular weight, (B) peak I, (C) peak II, (D) peak III.

FIG. 4 represents an SDS-PAGE analysis of phytolaccins purified by the immunoaffinity process of the invention. (A) protein standards of 68,000, 40,000 and 31,000 daltons, (B) $phytolaccin_1$ eluted from an anti-$phytolaccin_1$- Sepharose column, (C) non-absorbed $phytolaccin_2$ from an anti-$phytolaccin_1$-Sepharose column, (D) $phytolaccin_1$ from the conventionally-purified preparation shown in FIG. 1D, (E) co-chromatography of samples in lanes B and C, (F) co-chromatography of samples in lanes B and D.

FIG. 5 represents an ouchterlony antigen-antibody analysis of phytolaccin proteins. Phytolaccin proteins and their antibodies were purified by the immunoaffinity process of the invention. (A) wells #1, 2 and 3 contained 10 $\mu g$, 2 $\mu g$ and 0.5 $\mu g$ of $phytolaccin_1$, respectively; wells #4 and #5 contained 2 $\mu g$ and 0.5 $\mu g$ of $phytolaccin_2$, respectively; well #6 was blank and well #7 contained 20 $\mu g$ of anti-$phytolaccin_1$ antibody. (B) wells #1 through #6 were the same as in A; well #7 contained 10 $\mu g$ of anti-$phytolaccin_2$ antibody protein.

FIG. 6 includes toxicity data for immunoaffinity-purified $phytolaccin_1$-treated mice, consecutive day administration over 4 days.

BEST MODE FOR CARRYING OUT THE INVENTION

According to the process of the invention, $phytolaccin_1$ may be purified from plant extracts or mixtures of phytolaccin proteins. A small amount of purified $phytolaccin_1$ is coupled with activated Sepharose. Subsequently, purified $phytolaccin_1$ is introduced into a host organism to produce anti-$phytolaccin_1$ antibodies. The anti-$phytolaccin_1$ is then purified by contacting it with the $phytolaccin_1$-Sepharose column. The purified anti-$phytolaccin_1$ is then coupled with activated Sepharose. A Phytolacca plant extract or mixture of phytolaccin proteins is contacted with the anti-phytolaccin$_1$-Sepharose column and purified phytolaccin$_1$ is obtained. This process may similarly be used to obtain purified -phytolaccin$_2$ from a Phytolacca plant extract or mixture of phytolaccin proteins by using an initial feed of phytolaccin$_2$.

IMMUNOAFFINITY PURIFICATION OF PHYTOLACCIN PROTEINS

In the process detailed in the following sections, *Phytolacca americana* plants were harvested locally. The sources of other materials used were as follows:

| Material | Source |
| --- | --- |
| Affinity chromatography media | Pharmacia, Inc. |
| Diethylaminoethyl cellulose | Sigma Chemical Co. |
| Phosphocellulose | |
| Ammonium sulfate | |
| Lactoperoxidase | |
| Nucleotides | |
| Sodium thiocyanate | Aldrich Chemical Co. |
| Radiochemicals | Amersham Radiochemial Corp. |
| Gel electrophoresis supplies | Biorad Laboratories |
| Ultrapure sucrose | Bethesda Research Laboratories, Inc. |
| Tris | |

PREPARATION OF THE PHYTOLACCIN$_1$ ANTIBODY AFFINITY COLUMN

Preparation of Phytolaccin$_1$-Sepharose

Phytolaccin$_1$ was obtained from the leaves of young, pre-flowering *Phytolacca americana* plants which contained phytolaccin$_1$, but no phytolaccin$_2$ protein, using a protein purification technique described by Irvin, J. D. *Arch Biochem. Biophys.*, Vol. 169, pp. 522–528 (1975). A small amount of phytolaccin$_1$, purified by conventional ion-exchange liquid chromatography, was required to raise antibodies to phytolaccin$_1$ and for preparation of phytolaccin$_1$-Sepharose to be used in the isolation of the monospecific antibody from rabbit serum. Following purification of the leaf homogenate (FIG. 1A) on DEAE-cellulose (FIG. 1C) and phosphocellulose (FIG. 1D) columns, a single protein having a molecular weight of approximately 25,000 daltons was obtained which exhibited inhibitory activity against cell-free protein biosynthesis. Based on the amount of protein (1 unit) required to inhibit protein synthesis 50% in a reticulocyte lysate assay system, the product shown in FIG. 1D displayed a specific activity of approximately $2 \times 10^6$ units/mg protein. This value was ten times higher than that previously reported for similar preparations, see Irvin, supra; confirming the conclusion that phytolaccin is a more potent inhibitor of natural mRNA-dependent, rather than poly (U)- dependent, protein synthesis, Obrig, T. G., Irvin, J. D., and Hardesty, B. *Arch. Biochem. Biophys.*, Vol. 155, pp. 278–289.

Prior to coupling to Sepharose, the protein was analyzed for electrophoretic purity and monitored for biological activity. Attachment of phytolaccin$_1$ to Sepharose was carried out as follows. Three grams of cyanogen bromide-activated Sepharose 4B was swollen in 90 ml of 1 mM HCl for 30 minutes at 4° C. This mixture was washed with $3 \times 100$ ml 1 mM HCl in a scintered glass (coarse) funnel at room temperature. The swollen Sepharose was then washed with $3 \times 25$ ml of chilled PBS solution (0.02 M sodium phosphate, pH 7.4, 0.14 M sodium chloride) and transferred to a conical glass tube containing 20 ml of PBS solution. To this mixture was added 2 ml of phytolaccin protein solution (5 mg/ml in PBS) and the contents reacted at 4° C. for 16 hours, with gentle mixing. Coupled phytolaccin$_1$-Sepharose was collected on a scintered glass filter while the effluent was monitored for unreacted phytolaccin$_1$ protein. Coupling of phytolaccin$_1$ to Sepharose routinely was greater than 98% efficient. Phytolaccin$_1$-Sepharose, on the filter, was washed with $3 \times 50$ ml of PBS solution, resuspended in 100 ml of 0.2 M glycine, 0.01 M sodium phosphate, PH 7.5 and incubated for 5 hours at 4° C. to eliminate residual free cyanogen bromide. Subsequently, the phytolaccin$_1$-Sepharose was filtered as above, washed with $3 \times 50$ ml of PBS solution, pH 7.0, resuspended in this solution and packed into a $1.5 \times 7.0$ cm column.

Production and Affinity Purification of Anti-Phytolaccin

Phytolaccin$_1$, as obtained above, was utilized for the production of antibodies in New Zealand white rabbits. Animals were inoculated intradermally every 10th day with 100 μg of phytolaccin$_1$ in complete Freund's adjuvant. Complete Freund's adjuvant mixture consisted of 9 vols of mineral oil, 1 vol of mannide monoleate and 0.5 ng/ml of *Mycobacterium tuberculosum*. The adjuvant mixture was combined with an equal volume of 0.5 mg/ml phytolaccin$_1$ in 0.28 M NaCl, so that each 1 ml dose would deliver 100 μg of phytolaccin$_1$. Animals were bled from the lateral ear vein seven days after inoculation. Whole blood was allowed to clot at 20° C., centrifuged at 5,000 g/15 min and the supernatant serum was stored at −20° C. until needed.

Anti-phytolaccin$_1$ was purified from rabbit serum by absorption to phytolaccin$_1$-Sepharose. Fifty ml of serum was mixed with an equal vol of 1 M NaCl and applied to a 10 ml column of phytolaccin$_1$-Sepharose which had been equilibrated with PBS solution, pH 7.0 containing a 0.5 M NaCl. The column was washed with this high-KCl PBS solution to remove unbound material until the absorbance of the effluent was less than 0.001 A$_{280}$, as detected with an ISCO monitor. Bound anti-phytolaccin$_1$ was recovered by passing 17 ml of 3.5 M sodium isothiocyanate in PBS solution through the column. One ml fractions were collected into an equal volume of water, pooled and dialyzed against $3 \times 100$ vols of 0.14 M NaCl. The purity of affinity-purified antibody was measured with SDS-PAGE (sodium dodecyl sulfate polyacrylamide gel electrophesis) and the ouchterlony technique. Anti-phytolaccin$_1$ protein was crosslinked to cyanogen bromide-activated Sepharose using the methods described above.

USE OF THE PHYTOLACCIN ANTIBODY AFFINITY COLUMN TO PURIFY PHYTOLACCIN$_1$ PROTEIN

Affinity Purification Of Phytolaccin$_1$

Phytolaccin$_1$ was purified from a crude mixture using anti-phytolaccin$_1$-Sepharose chromatography. Leaves (450 9) of *Phytolacca americana* were blended in a commercial blender with 400 ml distilled-deionized water. The homogenate was passed through cheesecloth and centrifuged at 7,500 rpm/10 min in a type GSA (Beckman) rotor. The supernatant fraction was brought to 40% of saturation by slowly adding solid ammonium sulfate while stirring at 4° C. After stirring for 30 minutes, the preparation was centrifuged as above and additional ammonium sulfate was added to the supernatant fraction to 100% of saturation. Centrifugation was repeated and the resultant pellet was redissolved in approximately 180 ml of PBS solution. Following dialysis against 3×100 vols of PBS solution, the 40–100% ammonium sulfate fraction was stored at −20° C. until needed. Protein concentration was determined by the method of Lowry et al. *J. Biol. Chem.*, Vol. 193, pp. 265–271 (1951).

Approximately 800 mg of crude ammonium sulfate fraction protein in solution was adjusted to 0.5 M NaCl and applied to a 10 ml column of anti-phytolaccin$_1$-Sepharose. Elution of protein from the column was carried out with sodium isothiocyanate as described above. Eluate was dialyzed against 0.14 M NaCl, water and lyophilized. The affinity column was washed with PBS, pH 7.0 solution and stored at 4° C. with 0.1 mM merthiolate for future use. Phytolaccin$_1$, purified with this technique, was monitored as described below for biological activity in the reticulocyte lysate protein synthesis system and for homogeniety by SDS-PAGE. Purified antibody, reduced with $\beta$-mercaptoethanol and subjected to SDS-PAGE, is shown in FIG. 2(A) with two protein bands representing the 50,000 and 22,000 dalton subunits of IgG protein.

Figure 3:
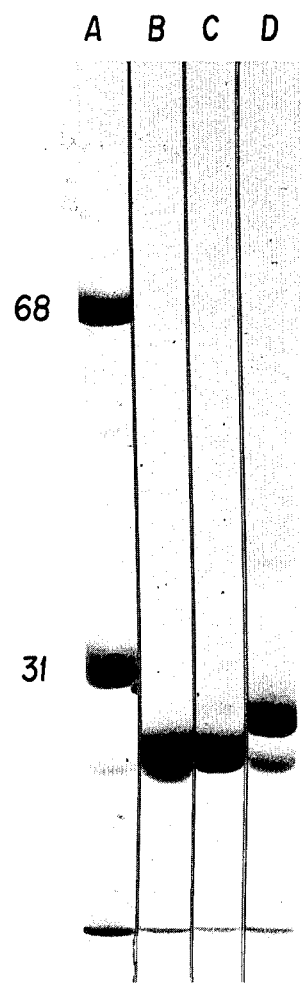

The utility of monospecific antibody-affinity columns in purification of both phytolaccin species from protein mixtures was studied. While conventional chromatographic procedures were capable of separating phytolaccins from other proteins, there remained a need for a simple method to further purify the two phytolaccin proteins from each other. For example, the use of conventional purification techniques to isolate phytolaccins from mature plants resulted in a set of heterogenous chromatographic products resolved as three biologically active peaks on a phosphocellulose column. These three fractions are shown in FIG. 3. The two earlier eluting peaks contained mostly phytolaccin$_1$, as represented in FIGS. 3B and 3C, respectively. The third peak consisted of a mixture of -phytolaccin proteins (FIG. 3D). A test was made of the antibody-affinity column to separate the two phytolaccins from the mixture shown in FIG. 3D using anti-phytolaccin$_1$-Sepharose. Material adsorbed to the affinity column was eluted with sodium isothiocyanate and analyzed by SDS-PAGE (FIG. 4B). Non-adsorbed protein (FIG. 4C) was shown to differ in size from the adsorbed material by co-chromatography of the two fractions (FIG. 4E). Further indication that the flow-through material was truly phytolaccin$_2$ was shown by co-chromatography of this fraction (FIG. 4C) with phytolaccin$_1$ obtained from young plants (FIGS. 1D and 4D), as show in FIG. 4F.

In other studies using this approach, phytolaccin$_2$ was purified from protein mixtures with immobilized antibody to phytolaccin$_2$.

A more rigorous test was made of the utility of antibody-affinity columns by purification of phytolaccins from leaf homogenates. An ammonium sulfate fraction (FIG. 1B) was applied to a phytolaccin$_1$ antibody-Sepharose column and eluted with sodium isothiocyanate, according to the process described above. The resulting fraction appeared, by SDS-PAGE analysis, to be a single 25,500 dalton protein species (FIG. 2B) corresponding to phytolaccin. Application of this procedure resulted in recovery of approximately 15–20 mg of phytolaccin$_1$ protein from 450 g (wet weight) of leaves. An antibody affinity column of this type, if washed with PBS solution after use, was routinely utilized at least 10 times without loss of binding activity.

The biological, immunological and physical characteristics of the affinity-purified phytolaccin proteins obtained according to the method described above were subsequently studied.

Antigenic Properties Of Immunoaffinity-Purified Phytolaccins

Figure 5A:
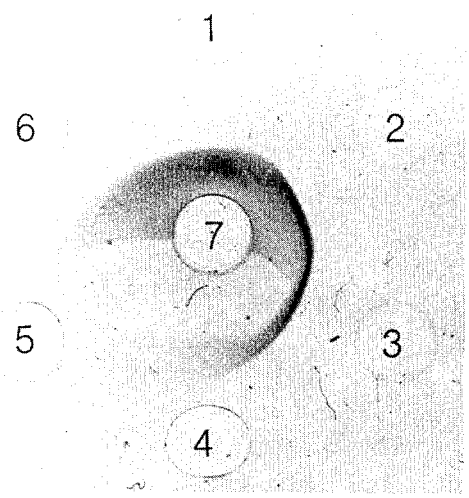
Figure 5B:
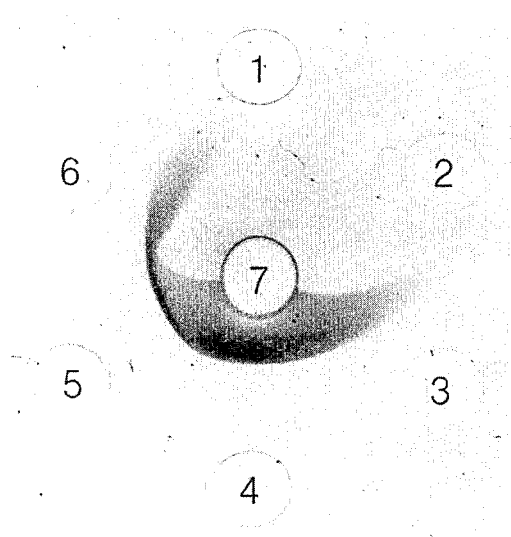

Antigen-antibody reactions were studied using ouchterlony gels stained with azocarmine red. Antibodies produced in rabbits against the phytolaccin species were shown to have little or no cross-reactivity with the opposite phytolaccin antigen. As shown in FIG. 5A, affinity-purified anti-phytolaccin$_1$ formed distinct precipitin bands with affinity-purified phytolaccin$_1$, but not with an equal or greater amount of pure phytolaccin$_2$. Similarly, affinity-purified anti-phytolaccin$_2$ reacted with affinity-purified Phytolaccin$_2$, but not with phytolaccin$_1$ (FIG. 5B). Antibodies against phytolaccin$_1$ and -phytolaccin$_2$ did not cross-react with the heterologous antigen, indicating a structural dissimilarity between the proteins. In these cases, it appeared that the species are immunologically distinct. Other results indicated that the lack of cross-reactivity was not due to interference of precipitation by any of the components. That is, diffusion of phytolaccin$_1$ or its antibody into the agarose area occupied by phytolaccin$_2$ and its antibody did not prevent visible precipitation of the latter components.

Figure 4:
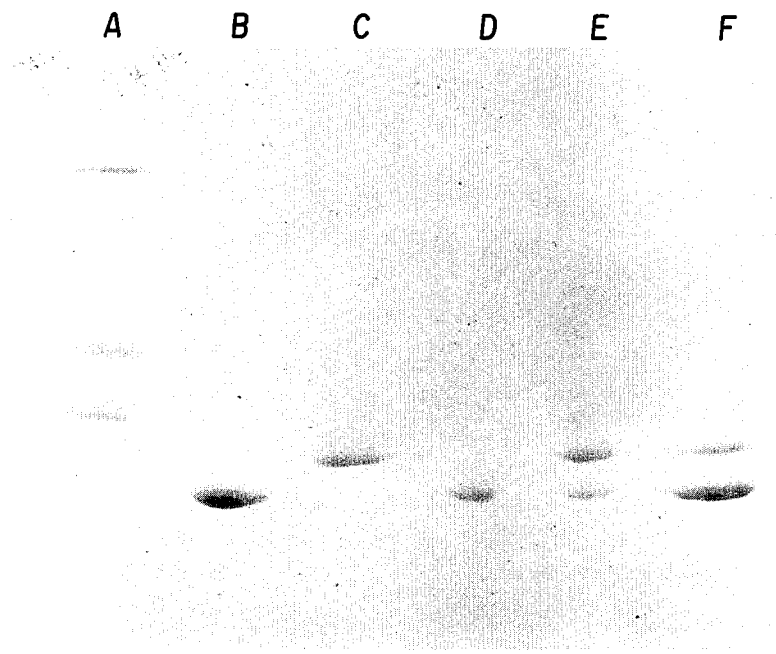

These results indicate that phytolaccin$_1$ and phytolaccin$_2$ are immunologically distinct entities even though apparent similarities of the proteins exist with respect to molecular mass, biological activity and physical characteristics. The observation that the phytolaccin$_1$ and phytolaccin$_2$ forms of the protein were not cross-reactive in antibody responses is a significant one. The two agents could, therefore, be therapeutically presented in sequence in order to avert neutralization of the agents by antibodies produced by host organisms receiving the agents for systemic treatment. Sequential introduction of the agents would be advantageous because therapeutic schedules could be extended for a prolonged course of treatment.

Physical Characteristics of Immunoaffinity-Purified Phytolaccins

A comparison was made of molecular weights for phytolaccin, as determined from equilibrium sedimentation and SDS-PAGE studies. Equilibrium sedimentation analysis of phytolaccin$_1$ indicated a tendency for self-association of the monomers to dimers at protein concentrations above 0.2 mg/ml. When subjected to equilibrium sedimentation analysis, phytolaccin$_1$ appeared to be slightly smaller than when examined under denaturing conditions in the SDS-PAGE system. The molecular mass of phytolaccin$_1$, as calculated from FIGS. 1–4, ranged from 24,500 to 26,300, with an average of 25,600 daltons. As indicated above, this average value is approximately 7% larger than the molecular mass obtained from equilibrium sedimentation studies, but 5 to 11% smaller than previously reported for phytolaccin$_1$, Irvin, J. D., *Arch. Biochem. Biophys.*, Vol. 169, pp. 522–528 (1975); Irvin, J. D., et al., *Arch. Biochem. Biophys.*, Vol. 200, pp. 418–425 (1980).

Analysis of protein products was conducted by electrophoresis in 10% polyacrylamide gels in the presence of sodium dodecyl sulfate as described by Laemmli, U.K., *Nature*, Vol. 277, pp. 680–685 (1970). Immunoaffinity-purified phytolaccin$_1$ and phytolaccin$_2$ were determined by denaturing gel electrophoresis to be approximately 25,600 and 28,400 daltons, respectively. However, data shown in FIGS. 3 and 4 are in agreement with an earlier study which indicated that phytolaccin$_2$ is approximately 7% larger than phytolaccin$_1$, Irvin, J. D., Kelley, T. and Robertus, J. D. Arch. Biochem. Biophys., Vol. 200, pp. 418–425 (1980). Taken together, these data suggest that immunoaffinity-isolated phytolaccin$_1$, resembles the conventionally purified protein and that phytolaccin$_1$ is closely related in size to phytolaccin$_2$. Comparative high-order UV derivative spectral analysis also indicated that phytolaccin$_1$ and phytolaccin$_2$ are structurally similar.

Biological Activity Of Immunoaffinity-Purified Phytolaccins

The immunoaffinity-purified phytolaccin species were found to be active, equally potent inhibitors of eukaryotic cell-free protein biosynthesis. In a study of the dose-response effect of the phytolaccins on [$^3$H]leucine incorporation into reticulocyte lysate protein, data taken during linear incorporation of $^3$H]leucine into protein indicated that phytolaccin$_1$ and phytolaccin$_2$ have an inhibition dose, ID$_{50}$, of approximately 0.4 nM and approximately 2 nM, respectively. ID$_{50}$ values obtained using different lysate and phytolaccin preparations indicate that both phytolaccin species were in the 0.1 nM to 4 nM range, with phytolaccin$_1$ usually being of equal or greater potency than phytolaccin$_2$.

An initial report on phytolaccin mode of action, Obrig, T. G., Irvin, J. D., and Hardesty, B., Arch. Biochem. Biophys., Vol. 155, pp. 278–289 (1973), indicated a similar activity of phytolaccin in a partially purified reticulocyte cell-free protein synthesis system. At that time, it was proposed that phytolaccin had, as its primary target, the ribosome. Further, the molar stoichiometry of phytolaccin to ribosome required for inhibition of protein synthesis suggested that the phytolaccin was of an enzymatic nature. In the present case, an estimation was made of phytolaccin to ribosome stoichiometry considering (1) that 1 ml lysate prepared from reticulocytosed rabbit blood contained 17A$_{260}$ of 80S ribosomes (2) that 12A$_{260}$ units of ribosomes was equivalent to 1 mg or 250 pmol of 80S ribosomes (3) a 27,000 Mr of phytolaccin$_1$ and (4) and ID$_{50}$ and ID$_{90}$ values of phytolaccin$_1$ of 0.4 nM and 4.0 nM, respectively. Thus, 50% inhibition of $^3$H]leucine incorporation into lysate protein occurred at an immunoaffinity-purified phytolaccin to 80S ribosome molar ratio of 1:30, while 90% inhibition took place at a 1:3 molar ratio. These data suggest that phytolaccin possesses catalytic activity during ribosome inactivation and is in agreement with previous results obtained with phytolaccin purified by conventional methodology, Obrig, et al., supra.

Specificity of immunoaffinity-purified phytolaccin$_1$ for inactivation of 60S ribosomal subunits is presented in Table 1.

TABLE 1

Effect of Phytolaccin on Ribosomal Subunit Activity in Polyphenylalanine Synthesis

| Subunit | Phenylalanine polymerized (pmol) | % of control |
|---|---|---|
| 40S + 60S | 4.6 | 100 |
| 40S* + 60S | 4.5 | 98 |
| 40S + 60S* | 0.9 | 20 |

TABLE 1-continued

Effect of Phytolaccin on Ribosomal Subunit Activity in Polyphenylalanine Synthesis

| Subunit | Phenylalanine polymerized (pmol) | % of control |
|---|---|---|
| 40S* + 60S* | 0.8 | 17 |

*Ribosomal subunit preincubated with 0.1 μM phytolaccin$_1$ as described. Phenylalanine incorporation with untreated 40S or 60S subunits was 0.1 and 0.3 pmol. respectively.

These data indicate that the larger (60S) ribosomal subunit is preferentially inactivated for protein synthesis when preincubated with phytolaccin, isolated and tested for support of poly(U)-directed polyphenylalanine synthesis. The precise mechanism of ribosome inactivation by phytolaccin remains to be elucidated. However, it easily determined earlier that phytolaccin-modified ribosomes were defective in the process of protein synthesis elongation, Obrig, et al., supra.

Analysis of polysomes in the lysate incubation mixture showed that immunoaffinity-purified phytolaccin$_1$, produced according to the invention, caused an accumulation of polysomes. This fact was indicative of a primary action at the level of peptide elongation vs. peptide initiation. Another characteristic which appeared to be shared by immunoaffinity-isolated and conventionally-purified phytolaccins was inactivity against whole reticulocyte protein biosynthesis (Table 2 and Obrig et al., supra.)

TABLE 2

Effect of Phytolaccin$_1$ on Protein Biosynthesis in Whole Rabbit Reticulocytes*

| Phytolaccin$_1$ (μM) | [$^3$H]leucine incorporation (cpm) |
|---|---|
| 0.001 | 10,530 |
| 0.01 | 10,370 |
| 0.1 | 10,560 |
| 1.0 | 10,450 |
| 10.0 | 10,100 |

*Whole reticulocytes were incubated with the indicated concentration of phytolaccin$_1$ for 10 min at 37° C. and [$^3$H]leucine incorporation monitored as described above.

These data suggest that phytolaccin did not rapidly enter whole reticulocytes. The effectiveness of the immunoaffinity-purified phytolaccin$_1$ appears to be attributed to its ability to penetrate virus-infected cells more efficiently.

Some unique aspects of immunoaffinity-purified phytolaccin were observed. The protein proved to be stable to high temperatures. Heat inactivation of phytolaccin$_1$ required a 5 minute incubation in PBS at 100° C. Such a treatment reduced protein synthetic inhibitory activity to less than 5% of control value, whereas a 2 min/100° C. incubation had no significant effect on biological activity of the protein.

It was also observed that exposure of phytolaccin$_1$ to a pH of 4.5 or 9.0 for 1 hour at 4° C., followed by dialysis against PBS solution, did not change the inhibitory activity, in vitro, of phytolaccin$_1$ for protein synthesis.

Figure 2:
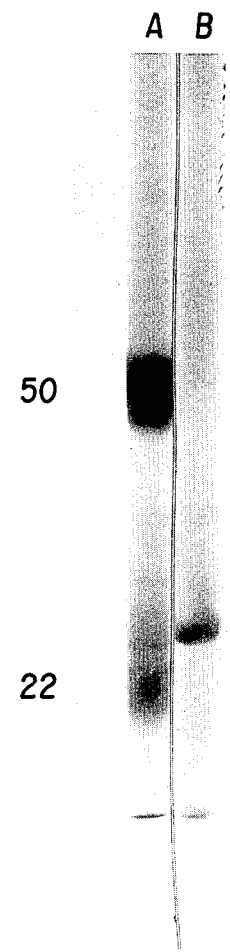

Monospecific antibodies against phytolaccin$_1$ did not interfere with the protein synthesis inhibitory activity of phytolaccin$_1$ in the reticulocyte lysate assay system. It should be emphasized that the phytolaccin$_1$ antibody and phytolaccin$_1$ antigen preparations were reactive on ouchterlony gels (FIG. 5A) and both were electrophoretically pure samples (FIG. 2). This result, indicating an absence of neutralizing activity by antibody, was confirmed in several experiments with six different amounts of antibody, ranging from an equimolar to a ten-fold molar excess of phytolaccin$_1$ antibody to phytolaccin$_1$ antigen. It was also observed that the monospecific antibody against phytolaccin$_2$ was without effect on the ability of phytolaccin$_2$ to inhibit protein biosynthesis, in vitro. Heterologous phytolaccin$_1$ and -phytolaccin$_2$ antibody-antigen combinations behaved in a similar fashion. The most direct explanation of these results is that monospecific antibodies prepared according to the process of the invention react with the antigen but do not alter the active site of the phytolaccin proteins.

Protein Synthesis Assays

To obtain reticulocytes, New Zealand white rabbits (2–2.5 kg) were injected daily, on days 1 through 4, with 0.25 ml/kg of 2.5% phenylhydrazine, pH 7.0, in 0.14 M NaCl. On the 7th day, rabbits were sacrificed and blood drained from the heart into a freshly prepared ice-cold NKM solution (0.14 M NaCl, 0.03 M KCl, 0.002 M $MgCl_2$) containing 200 units of heparin/ml. Reticulocytosis, as measured with methylene blue staining, was found to be 90% or higher. Whole blood was filtered through cheesecloth, centrifuged at 1,000×g/10 min and serum removed along with an upper "buffy coat" layer of cells. Packed reticulocytes were gently resuspended in 20 volumes of NKM solution and centrifuged as above. This washing procedure was repeated a total of three times, Hardesty et al., *Methods Enzymol.,* Vol. 20, pp. 316–330 (1971).

Lysate was prepared with the addition of 1 volume of glass-distilled deionized water to packed cells, followed by gentle shaking (4° C. for 10 min) and centrifugation at 20,000 ×g/15 min. Aliquots of the resultant supernatant were stored at −80° C. for up to one year, without loss of activity. When first employed, each batch of lysate was tested with varying quantities of hemin and magnesium acetate to determine concentrations required for maximum protein synthetic activity. Maximum rates of protein synthesis in the lysate system were very close to that of whole reticulocytes.

Incorporation of amino acids into protein with a lysate preparation was carried out in a total volume of 25 μl which contained: 0.02 M Tris-HCl, pH 7.4, 0.08M K(OAc), 2.0 mM $Mg(OAc)_2$, 1.0 mM ATP, 0.2 mM GTP, 130 μg creatine phosphate, 5.0 μg creatine phosphokinase, 0.05 mM each of 19 common amino acids minus leucine, 2.5 μCi of L-[4,5-$^3$H]leucine (SA =50 Ci/mmol), and 10 μl reticulocyte lysate containing 10 μg hemin. Following incubation at 37° C. for up to 45 minutes, the reaction was terminated with the addition of 100 μl of ice-cold water. The reaction stopped rapidly due to a combination of low temperature and reduced salt concentrations required for protein synthesis. Incorporation of [$^3$H]leucine into protein was measured by spotting 5 μl of assay solution on 1.5 cm squares of Whatman #1 filter paper and exposing the paper sequentially to: (1) 5% trichloroacetic acid/90° C./5 min, (2) acidified acetone/5 min, (3) 95% ethanol/5 min and (4) 100% ethanol/5 min. After drying the paper at 60° C./10 min, each sample was placed in a scintillation vial with 5 ml of a toluene based scintillation fluid and radioactivity monitored in a Beckman LS-100 counter. A background of 35 cpm observed in the absence of lysate has been subtracted from each value.

Incorporation of precursors into protein by whole rabbit reticulocytes was measured in aliquots of a mixture containing the following in a total volume of 3.2 ml: 6 mM Tris-HCl, pH 7.4, 4 mM KCl, 1.2 mM $MgCl_2$, 0.11 M NaCl, 0.06 mM $FeNH_4(SO_4)_2$, 0.06 mM each of 19 amino acids minus leucine, 0.1 ml rabbit plasma, 0.4 ml packed, washed reticulocytes and 20 μCi L-[4,5-3H-]leucine (SA=50 Ci/mmol). Following incubation of 0.1 aliquots at 37° C. for 10 min, the reaction was stopped with the addition of 0.6 ml of ice-cold NKM solution. Reticulocytes were pelleted at 700×g for 5 minutes in a Fisher Model 59 centrifuge and washed twice in cold NKM solution with centrifugation. Cells were lysed by incubation at 4° C./10 min with 0.3 ml water and centrifuged at 1,000×g for 5 minutes. A portion (0.10 ml) of the resultant supernatant was added to 0.5 ml of 5% trichloroacetic acid, heated at 90° C./10 min, cooled and centrifuged at 1,000 g for 5 minutes. After removal of the supernatant fraction, the pellet was dissolved in 0.2 ml of 0.2 M NaOH, reprecipitated with 0.3 ml acidified acetone, centrifuged, redissolved in 0.2 ml of 0.2M NaOH, treated with 0.3 ml of 10% trichloroacetic and centrifuged as above. Washed precipitated protein was again redissolved in 0.2 ml of 0.2M NaOH and 100 μl was transferred to a scintillation vial for counting in 10 ml of scintillation fluid (Hydromix, Yorktown Research, Hackensack, N.J.) after neutralization with 8 μl of glacial acetic acid.

Polyphenylalanine synthesis was measured with conditions previously described, Obrig et al., *Arch. Biochem. Biophys.,* Vol. 155, pp. 278–289 (1973); Obrig et al, *Eur. J. Biochem.,* Vol. 21, pp. 31–41 (1971). Procedures for the preparation of $^3$H]phenylalanyl-tRNA, elongation factors and ribosomal subunits were reported previously, Obrig et al., *Eur. J. Biochem.,* Vol. 21, pp. 31–41 (1971); Hardesty, *Methods Enzymol.,* Vol. 20, pp. 330–337 (1971). Polyribosomes were analyzed by layering 0.20 ml of reticulocyte lysate protein synthesis assay mixture onto a 4.8 ml gradient of 15 to 45% sucrose in 20 mM Tris-HCl, 70 mM KCl, 3 mM $MgCl_2$, 1 mM β-mercaptoethanol buffer solution. Following centrifugation at 49,000 rpm/75 min in a SW 50.1 rotor (Beckman), the contents were displaced with a 50% sucrose solution injected into the bottom of each tube and analyzed for absorbance at 260 nm.

The immunoaffinity-purified phytolaccin$_1$ and phytolaccin$_2$ were determined to have similar biological activity as inhibitors of protein synthesis and to be structurally related, as determined by high-order derivative spectroscopy. However, the absence of cross-reactivity of heterologous antigen-antibody couples strongly indicates the existence of independent antigenic domains in the two proteins. In addition, the monospecific antibody preparations appear to identify a portion of the antigens other than the putative enzymatic active sites.

Antiviral Activity of Immunoaffinity-Purified Phytolaccin$_1$ Against Herpes Simplex Virus Type II The in vivo systemic efficacy of phytolaccin$_1$ as a drug used for the treatment of Herpes Simplex Virus type II vaginal infections was studied in a murine model system, according to a multiple dose regimen. A virus solution was prepared by diluting Herpes Simplex Virus type II (Curtis strain) with media #199 with Hanks salts (Flow Laboratories) supplemented with 100 units of Pencillin G per milliliter and 100 micrograms of Streptomycin per milliliter, immediately prior to use. Immunoaffinitypurified phytolaccin$_1$ was prepared according to the method of the invention.

Herpes Simplex Virus type II infections were induced in non-pregnant, weaned, female Nylor mice (N.Y. State Health Labs) via intravaginal inoculation by means of a cotton pellet saturated with the virus solution. Treatment groups consisted of eight mice, weighing 9 to 11 grams each. Three different test groups were studied.

The Group III mice each received an intravaginal virus inoculation on day zero. A daily dose of 0.50 μg of phytolaccin$_1$ in a 0.20 ml volume of normal 0.14 molar saline solution, (50.0 μg/kg/day) was administered by intraperitoneal injection over the course of four consecutive days. The initial injection was administered approximately one hour after the viral inoculation.

The Group I mice also received intravaginal virus inoculations with the virus solution. Within approximately one hour of the inoculation, the first of four consecutive daily doses of a 0.20 ml volume of normal 0.14 molar saline solution was administered by intraperitoneal injection.

The Group II mice were not inoculated with the virus and received a daily dose of 0.50μg of phytolaccin$_1$ in a 0.20ml volume of normal 0.14 molar solution by intraperitoneal injection on four consecutive days.

Figure 6:
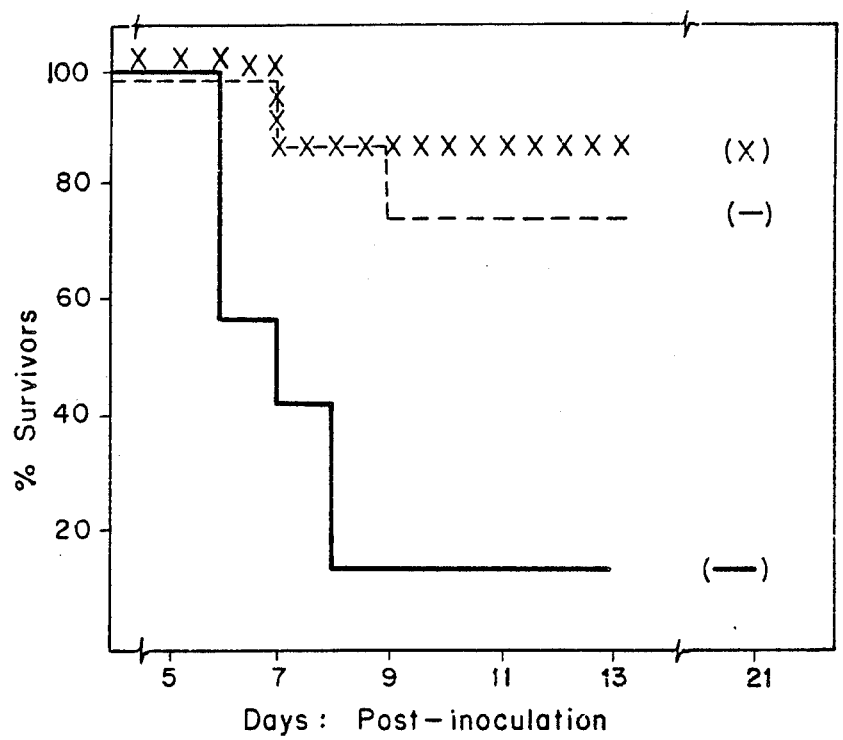

The antiviral activity data is shown in FIG. 6. Phytolaccin$_1$ was found to be 75% effective as an antiviral agent when administered in a multiple dose regimen of 50 μg/kg/day post-inoculation. At the dosage administered, 12% residual drug toxicity was present. In the Group III mice, symptoms of virus infection, including vaginitis, were reversed by the phytolaccin$_1$ agent and no recurrence of the infection was observed through day 21 after inoculation.

Whole animal toxicity effects of phytolaccin$_1$ were studied to estimate an approximate therapeutic index for a phytolaccin$_1$-based drug. Treatment groups consisted of non-pregnant, outbred CD-1 female mice (Taconic Farms). Six mice, each weighing approximately 25 grams, were part of each treatment group.

Lethality data was obtained by studying three groups of animals, each of which received a single 0.20 ml intraperitoneal injection of phytolaccin$_1$ in normal 0.14 molar saline solution on day 0. The dosages administered were as follows:

| Group I | 2.5 mg/kg |
| Group II | 5.0 mg/kg |
| Group III | 10 mg/kg. |

On the basis of the toxicity study, an LD$_{50}$ value of about 7.5 mg/kg body weight was estimated.

While all of the mice in the 2.5 mg/kg–10 mg/kg dosage groups exhibited some gastrointestinal distress problems, these disappeared completely in all the survivors.

A therapeutic index for the phytolaccin$_1$ antiviral agent was estimated. The therapeutic index values, represented in Table 3, were calculated from the results of the toxicology study (single dose administration) and the antiviral activity study (consecutive day administration over 4 days).

TABLE 3

| Therapeutic Index for Phytolaccin$_1$ Antiviral Agent | | |
| --- | --- | --- |
| Phytolaccin$_1$ Dosage* | 3.0 mg/kg** (LD$_{10}$ estimate) | 7.5 mg/kg** (LD$_{50}$ estimate) |
| 50 μg/kg (daily) | 60 | 150 |
| 200 μg/kg (4 days) | 15 | 37.5 |

*From antiviral activity data
**From toxicology data

The therapeutic index values listed above are better than or equal to the values of most anti-tumor drugs presently in clinical use. Dosages of phytolaccin$_1$ which are lower than the 50 μg/kg/day×4 day regimen may also result in antiviral activity with higher therapeutic index values for the agent.

Phytolaccin$_1$, purified according to the invention, may be diluted in any pharmaceutically acceptable solution or suspension to a therapeutically effective concentration.

The preferred mode of administration is by injection. The agent may also be combined with suitable adjuvants and administered in the form of a dermal or oral pharmaceutical.

In the treatment of Herpes Simplex type II host infections, the therapeuticallyeffective dose of the phytolaccin$_1$ antiviral agent will vary with the subject, as well as the method and regimen of administration.

If the desired mode of administration is by dermal application, for surface lesions, penetrability of the phytolaccin$_1$ agent would be increased by the reduction of physical size of the protein through enzymatic treatment. Reduction in size could also be effected by cloning the gene coding for the protein, generating DNA fragments coding for a smaller version of the agent. Once generated, the DNA fragments would be incorporated into a suitable vector and transcribed-translated in bacteria. The end result, as with proteolytic cleavage of phytolaccin$_1$, would be a smaller and more effective antiviral agent.

Phytolaccin may also be administered in combination with one or more antiviral agents which are characterized by different modes of action. The advantage of this type of treatment would be the circumvention of development of antiviral agent-resistant strains of the target pathogen, as well as effective treatment dosages in combination with other drugs.

Having described the invention with particular reference to the preferred form thereof, it will be obvious to those skilled in the art to which the invention pertains after understanding the invention, that various changes and modifications may be made therein without departing from the spirit and scope of the invention as defined by the claims appended hereto.

I claim:

1. An antiherpetic composition for the treatment of systematic Herpes Simplex Virus type II infection in mammals, comprising as an active ingredient, a therapeutically effective amount of phytolaccin protein, or fragment thereof, and a pharmaceutical carrier that is suitable for administration in vivo.

2. The antiherpetic composition according to claim 1 in which the phytolaccin protein comprises phytolaccin$_1$.

3. The antiherpetic composition according to claim 2 in which the phytolaccin$_1$ has an average molecular weight of between 24,500 and 26,300 daltons.

4. The antiherpetic composition according to claim 2 in which the phytolaccin$_1$ has an average molecular weight of about 25,600 daltons.

5. The antiherpetic composition according to claim 2 in which the phytolaccin$_1$ is immunoaffinity-purified.

6. The antiherpetic composition according to claim 1 in which the phytolaccin protein comprises phytolaccin$_2$.

7. The antiherpetic composition according to claim 6 in which the phytolaccin$_2$ has an average molecular weight of about 28,400 daltons.

8. The antiherpetic composition according to claim 6 in which the phytolaccin$_2$ is immunoaffinity-purified.

9. The antiherpetic composition according to claim 1 which further comprises one or more antiviral agents which are characterized by a non-phytolaccin mode of action.

10. The antiherpetic composition according to claim 2 which further comprises one or more antiviral agents which are characterized by a non-phytolaccin mode of action.

11. The antiherpetic composition according to claim 6 which further comprises one or more antiviral agents which are characterized by a non-phytolaccin mode of action.

* * * * *